United States Patent
Wang et al.

(10) Patent No.: US 11,161,811 B2
(45) Date of Patent: Nov. 2, 2021

(54) PROCESS FOR PREPARING MANNICH BASE QUATERNARY AMMONIUM SALT HIGH-TEMPERATURE RESISTANT CORROSION INHIBITOR AND APPLICATIONS THEREOF

(71) Applicant: SOUTHWEST PETROLEUM UNIVERSITY, Sichuan (CN)

(72) Inventors: Dingli Wang, Sichuan (CN); Yongming Li, Sichuan (CN); Xiyu Chen, Sichuan (CN); Youshi Jiang, Sichuan (CN); Juhui Zhu, Sichuan (CN)

(73) Assignee: SOUTHWEST PETROLEUM UNIVERSITY, Sichuan (CN)

( * ) Notice: Subject to any disclaimer, the term of this patent is extended or adjusted under 35 U.S.C. 154(b) by 150 days.

(21) Appl. No.: 16/622,832

(22) PCT Filed: Nov. 20, 2018

(86) PCT No.: PCT/CN2018/116448
§ 371 (c)(1),
(2) Date: Dec. 13, 2019

(87) PCT Pub. No.: WO2020/093444
PCT Pub. Date: May 14, 2020

(65) Prior Publication Data
US 2020/0331856 A1    Oct. 22, 2020

(30) Foreign Application Priority Data
Nov. 7, 2018  (CN) .......................... 201811320918.9

(51) Int. Cl.
| C07D 209/08 | (2006.01) |
| C07D 333/22 | (2006.01) |
| C07D 211/14 | (2006.01) |
| C09K 8/54 | (2006.01) |
| C09K 8/74 | (2006.01) |

(52) U.S. Cl.
CPC .......... *C07D 209/08* (2013.01); *C07D 211/14* (2013.01); *C07D 333/22* (2013.01); *C09K 8/54* (2013.01); *C09K 8/74* (2013.01)

(58) Field of Classification Search
None
See application file for complete search history.

(56) References Cited

U.S. PATENT DOCUMENTS

| 3,514,465 A | * | 5/1970 | Posselt | C07D 231/28 546/328 |
| 3,523,952 A | * | 8/1970 | Orth | C07D 207/337 548/561 |
| 4,071,327 A | * | 1/1978 | Dorer, Jr. | C10L 1/2225 252/393 |
| 4,137,164 A | * | 1/1979 | Coscia | C08F 8/44 210/734 |
| 4,141,827 A | * | 2/1979 | Coscia | C02F 1/54 210/734 |
| 4,374,256 A | * | 2/1983 | Kao | C07D 207/337 548/561 |
| 7,112,559 B1 | * | 9/2006 | Mayhall | A01N 33/12 510/130 |
| 7,842,127 B2 | | 11/2010 | Malwitz | |
| 8,980,887 B2 | * | 3/2015 | Yang | A61P 25/08 514/233.2 |
| 2013/0203754 A1 | * | 8/2013 | Yang | A61P 25/22 514/233.2 |

FOREIGN PATENT DOCUMENTS

| CN | 103289663 A | 9/2013 |
| CN | 105154049 A | 12/2015 |
| CN | 105419774 A | 3/2016 |
| CN | 108753271 A | 11/2018 |
| WO | WO2018111230 | 6/2018 |

* cited by examiner

*Primary Examiner* — Joseph D Anthony
(74) *Attorney, Agent, or Firm* — Muncy, Geissler, Olds & Lowe, P.C.

(57) ABSTRACT

The present invention discloses a process for preparing a Mannich base quaternary ammonium salt high-temperature resistant corrosion inhibitor and applications thereof. The preparation process comprises the following steps: (1) dissolve an amine substance indole, benzhydrylpiperidine, diphenylethylamine, dibenzylamine or diisopropanolamine into an organic solvent, slowly add an aldehyde substance 3-(2-thienyl)benzaldehyde or cinnamaldehyde, then place in a constant-temperature water bath, stir to react at 60-80° C. for 1 to 3 hours, then add a ketone substance benzalacetone, diphenylstyryl acetone or 1,1-diphenylacetone, adjust the reaction system pH to 3 to 4 using a hydrochloric acid solution, and then react for 7 to 10 hours; after cooled to room temperature, perform distillation under a reduced pressure to remove the solvent, to obtain a Mannich base; (2) dissolve the Mannich base in an organic solvent, add quaternizing reagent chloromethylnaphthalene, benzyl chloride or triphenylchloromethane, then react at 70-90° C. for 14-16 h, after cooled to room temperature, perform distillation under a reduced pressure. The process is simple and feasible, and its raw material is non-toxic, safe and environmental-friendly, and the prepared corrosion inhibitor has obvious resistance to the acid corrosion of carbon steels in oil-gas wells.

4 Claims, No Drawings

PROCESS FOR PREPARING MANNICH BASE QUATERNARY AMMONIUM SALT HIGH-TEMPERATURE RESISTANT CORROSION INHIBITOR AND APPLICATIONS THEREOF

TECHNICAL FIELD

The present invention relates to a process for preparing Mannich base quaternary ammonium salt high-temperature resistant corrosion inhibitor in the field of corrosion inhibitor materials and applications thereof.

BACKGROUND ART

In the production-increasing and upgrading of oil-gas field, fracture acidification has become the mainstream method for the oil-gas field. In the acid fracturing process, the injection of acid liquid can remove the blockage of the oil and gas wellbore and stratum to a great extent and improve the matrix permeability, thereby increasing the oil and gas recovery. However, the acidification construction will also bring many problems to the oil fields. In the acidification construction process, the injection of acid liquid such as hydrochloric acid may cause corrosion of oil and gas well strings, construction pipelines and metal equipment, and in severe cases, it may lead to sudden fracture accidents of downhole pipes and pipeline perforation, with potential safety hazards; in addition, the metal iron ions that are corroded by the acid solution may cause damage to the stratum. In order to prevent acid liquid from corroding oil pipes, casing and construction equipments, it is necessary to add a corrosion inhibitors to the acid liquid, which is the most commonly used and effective anti-corrosion measure. At present, most of the commercially available corrosion inhibitors have the drawbacks of easy coking, delamination, unstable dissolution and dispersion properties, toxic raw materials, flammability and explosiveness, and heavy contamination, etc.

In the invention titled "an alkynyl Mannich base corrosion inhibitor and synthesis process and applications thereof" (201610436640.6), by improving the raw materials, ratios, process steps of key synthesis process of corrosion inhibitors, the non-toxic, environment-friendly corrosion inhibitors are prepared, with better corrosion inhibition effect and high temperature resistance, especially suitable for use as a hydrochloric acid corrosion inhibitor in pickling carbon steels. However, the raw material propargyl alcohol used is highly toxic, flammable and explosive and highly corrosive.

In the invention titled "a highly water-soluble and high-temperature resistant Mannich base corrosion inhibitor intermediate and preparation process thereof" (201410086970.8), when any solvent is not applicable and only in the presence of alkali metal alkoxide catalyst, aldehyde, ketone, amine condensates react with the hydrophilic surfactant to obtain a highly water-soluble and high-temperature resistant Mannich base corrosion inhibitor intermediate. Because no solvent is used, the drawbacks of low product content or difficulty in recycling caused by the use of solvents are solved, and poor water solubility and easy decomposition at high temperature of other corrosion inhibitors are solved, and the inconvenience to the production caused by toxic substances is reduced; and in addition, the acidic corrosion of high temperature hydrochloric acid can be inhibited. However, the alkali metal alkoxides used such as sodium methoxide are sensitive to oxygen, flammable and explosive and highly corrosive.

In the invention titled "a triazole-modified Mannich base compound and preparation process thereof" (201610073911.6), a triazole-modified Mannich base corrosion inhibitor is prepared by Mannich reaction, epoxidation reaction of ketone, and ring-opening reaction of ether. Because Mannich base is a corrosion inhibitor molecule with N and O atoms as active centers, the lone pair electrons can be complexed with metal ions in the form of coordination bonds to form a polymer, and can be combined with metal atoms to cover the equipment surface in a form of an adsorption film, playing a role of corrosion inhibition. However, the raw material lithium hydroxide is a highly toxic substance and requires high preparation technology, which is not conducive to the safety production and environmental protection.

Therefore, it is of great significance to develop a new type of high-temperature-resistant corrosion inhibitor with simple formula, mild synthesis conditions, non-toxicity and safety, environmental protection and meeting the rigor requirements of the current acidification construction of oil-gas wells.

SUMMARY OF THE INVENTION

An object of the present invention is to provide a process for preparing a Mannich base quaternary ammonium salt high-temperature resistant corrosion inhibitor and applications thereof. The process is simple and feasible, and the prepared corrosion inhibitor has good corrosion resistance at high temperature; in addition, its raw material is non-toxic, safe and environmental-friendly. When the quaternary ammonium salt corrosion inhibitor is used as an oil-gas well acidizing corrosion inhibitor, it has good solubility in hydrochloric acid solution and can significantly inhibit the acid corrosion of carbon steels in oil-gas wells.

In order to achieve the foregoing technical object, the present invention adopts the following technical solutions:

A process for preparing a Mannich base quaternary ammonium salt high-temperature resistant corrosion inhibitor, comprising the following steps in sequence:

(1) Dissolve an amine substance indole, benzhydrylpiperidine, diphenylethylamine, dibenzylamine or diisopropanolamine into an organic solvent, slowly add an aldehyde substance 3-(2-thienyl)benzaldehyde or cinnamaldehyde, then place in a constant-temperature water bath, stir to react at 60-80° C. for 1 to 3 hours, then add a ketone substance benzalacetone, diphenylstyryl acetone or 1,1-diphenylacetone at a certain ratio, adjust the reaction system pH to 3 to 4 using a hydrochloric acid solution, and then react for 7 to 10 hours; after cooled to room temperature, perform distillation under a reduced pressure to remove the solvent, to obtain a Mannich base;

(2) Dissolve the Mannich base in an organic solvent, add quaternizing reagent chloromethylnaphthalene, benzyl chloride or triphenylchloromethane at a certain ratio, then react at 70-90° C. for 14-16 hours. After cooled to room temperature, perform distillation under a reduced pressure to give the Mannich base quaternary ammonium salt high-temperature resistant corrosion inhibitor.

Further, the molar ratio of amine substance, aldehyde substance and ketone substance is 1:1:1-1:1:2 in the step (1).

Further, the organic solvent is ethanol or acetonitrile.

Further, the molar ratio of Mannich base to quaternizing reagent in step (2) is 1:1-1:2.

Applications of the Mannich base quaternary ammonium salt high-temperature resistant corrosion inhibitor means that the corrosion inhibitor is used as an oil-gas well corrosion inhibitor, to show a significant inhibitory effect on the acid corrosion of carbon steels in oil-gas wells because of its good dispersibility and solubility in acid solutions.

The specific reaction process of the acidizing corrosion inhibitor is as follows:

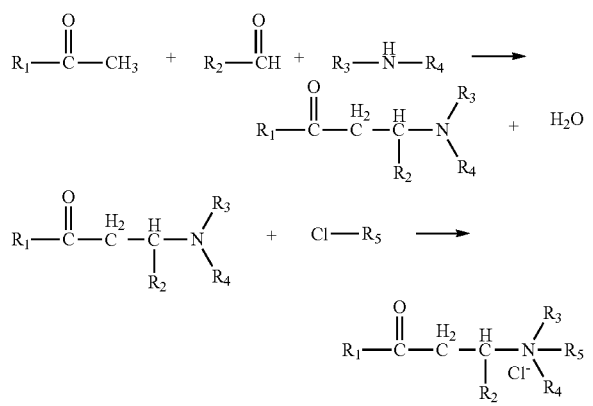

The preparation process of the invention is simple, and its mechanism is as follows: the compounds having active α-H, such as aldehydes and ketones, are refluxed with aldehydes and amines in a solution such as ethanol, so that α-H of the ketone is substituted by an amine methyl group, to have an amine methylation reaction. First, the carbonyl group is protonized, and the amine and carbonyl group have a nucleophilic addition reaction, to remove proton and transfer the electrons on the nitrogen, then the water is removed, to obtain an imine ion intermediate. The imine ion, as an electrophile, attacks the enol-type structure containing active hydrogen compounds, to lose protons and give the product Mannich base. The Mannich base quaternary ammonium salt prepared by the present invention contains polar groups such as carbonyl and amino, etc., he nitrogen and oxygen atoms contain unshared electrons, which can enter the empty orbits of iron atoms to form coordination bonds, making the corrosion inhibitor molecules to be adsorbed on the metal surface. In order to make the corrosion inhibitor to strongly adsorb on the metal surface, the π bond is added for adsorption, that is, the corrosion inhibitor molecule contains π bond or large π bond, and electrons enter the empty orbits of the metal atoms to form π bond adsorption and tightly adsorb on the iron to inhibit its corrosion; in addition, multiple hydroxyl groups in the corrosion inhibitor molecule can greatly improve the dispersibility of the corrosion inhibitor and its solubility in acid solution.

DETAILED DESCRIPTION OF THE PREFERRED EMBODIMENTS

The present invention is further described in conjunction with the following embodiments.

Embodiment 1

A process for preparing a Mannich base quaternary ammonium salt high-temperature resistant corrosion inhibitor, comprising the following steps:

(1) Add 1.97 g of dibenzylamine to a 250 mL three-necked flask, then slowly add 1.88 g of 3-(2-thienyl) benzaldehyde, and add 70 mL of absolute ethanol as a solvent at the same time and stir them well, and place the reaction system to a thermostatic water bath to react at 70° C. for 1 h while stirring;

(2) Add 1.46 g of benzalacetone to the flask, adjust the pH of the reaction system to 4 using a hydrochloric acid solution, and react for 8 hours. After cooled to room temperature, remove the solvent by distillation under reduced pressure, to obtain a Mannich base;

(3) Add 5.13 g of the above Mannich base product to a 250 mL three-necked flask, add 110 mL of absolute ethanol as a solvent and stir them well, slowly add 1.27 g of benzyl chloride and stir well, and stir at 80° C. to react for 12 h, after cooled to room temperature, perform distillation under a reduced pressure to give the Mannich base quaternary ammonium salt corrosion inhibitor.

The nitrogen atoms on the raw materials benzalacetone and dibenzylamine used in this embodiment have high activity. Under the above reaction conditions, the obtained quaternary ammonium hydrochloride corrosion inhibitor has good corrosion inhibition performance.

The specific reaction process of the above preparation process is as follows:

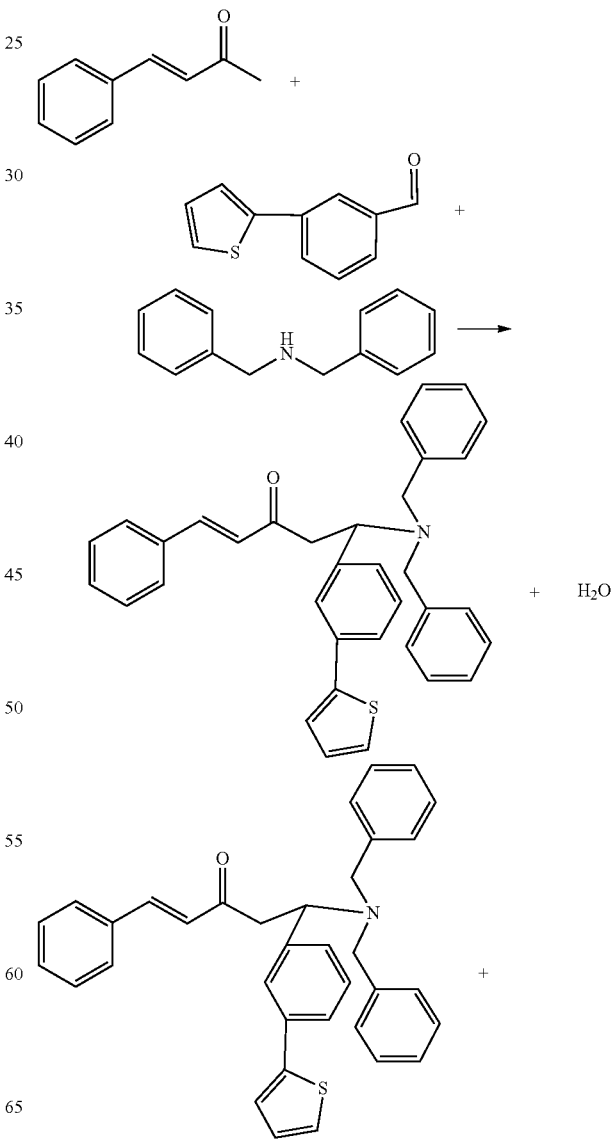

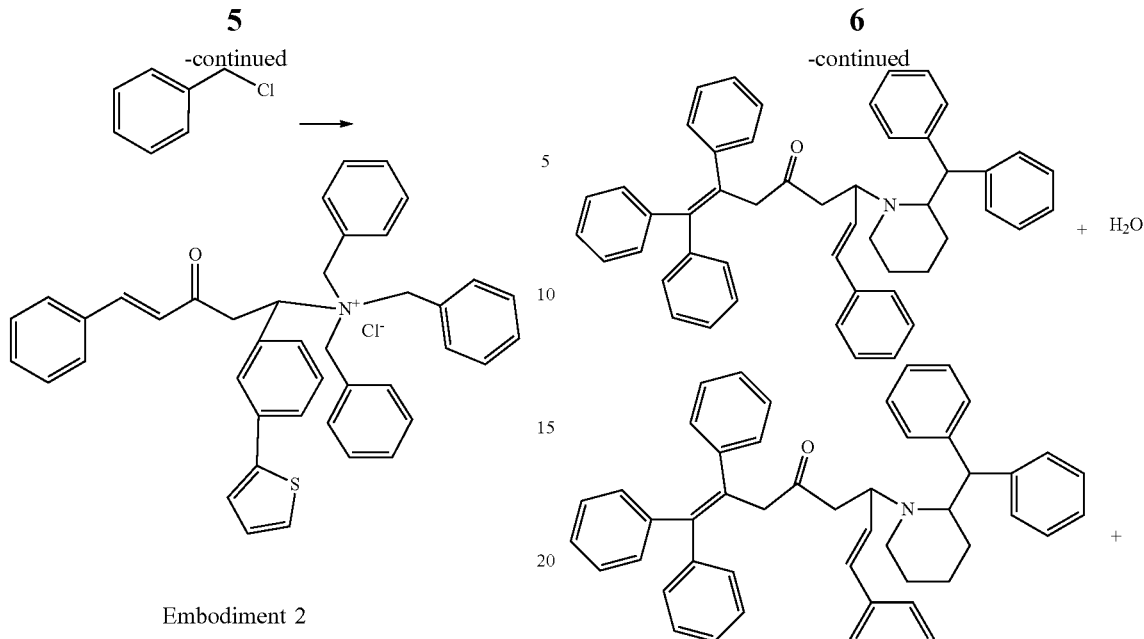

Embodiment 2

A process for preparing a Mannich base quaternary ammonium salt high-temperature resistant corrosion inhibitor, comprising the following steps:

(1) Add 2.51 g of benzhydrylpiperidine to a 250 mL three-necked flask, then slowly add 1.32 g of cinnamaldehyde, and add 100 mL of absolute ethanol as a solvent at the same time and stir them well, and place the reaction system to a thermostatic water bath to react at 70° C. for 1 h while stirring;

(2) Add 3.12 g of diphenylstyryl acetone to the flask, adjust the pH of the reaction system to 4 using a hydrochloric acid solution, and react for 8 hours. After cooled to room temperature, remove the solvent by distillation under reduced pressure, to obtain a Mannich base;

(3) Add 6.77 g of the above Mannich base product to a 250 mL three-necked flask, add 120 mL of acetonitrile as a solvent and stir them well, slowly add 1.76 g of chloromethylnaphthalene and stir well, and stir at 85° C. to react for 12 h, after cooled to room temperature, perform distillation under a reduced pressure to give the Mannich base quaternary ammonium salt corrosion inhibitor.

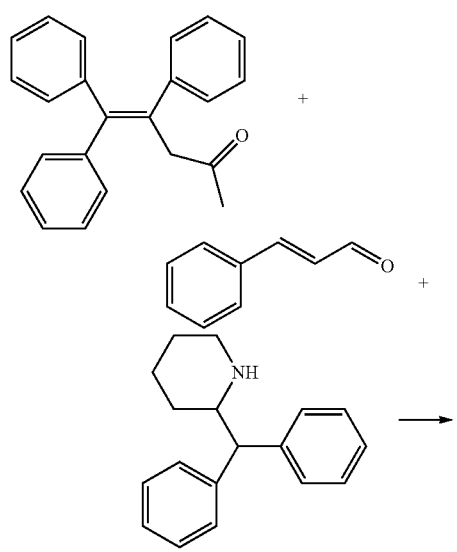

Embodiment 3

A process for preparing a Mannich base quaternary ammonium salt high-temperature resistant corrosion inhibitor, comprising the following steps:

(1) Add 1.17 g of indole to a 250 mL three-necked flask, then slowly add 1.32 g of cinnamaldehyde, and add 90 mL of absolute ethanol as a solvent at the same time and stir them well, and place the reaction system to a thermostatic water bath to react at 80° C. for 1 h while stirring;

(2) Add 1.46 g of benzalacetone to the flask, adjust the pH of the reaction system to 3 using a hydrochloric acid solution, and react for 9 hours. After cooled to room temperature, remove the solvent by distillation under reduced pressure, to obtain a Mannich base;

(3) Add 3.77 g of the above Mannich base product to a 250 mL three-necked flask, add 110 mL of absolute ethanol as a solvent and stir them well, slowly add 2.78 g of triphenylchloromethane and stir well, and stir at 80° C. to react for 13 h, after cooled to room temperature, perform distillation under a reduced pressure to give the Mannich base quaternary ammonium salt corrosion inhibitor.

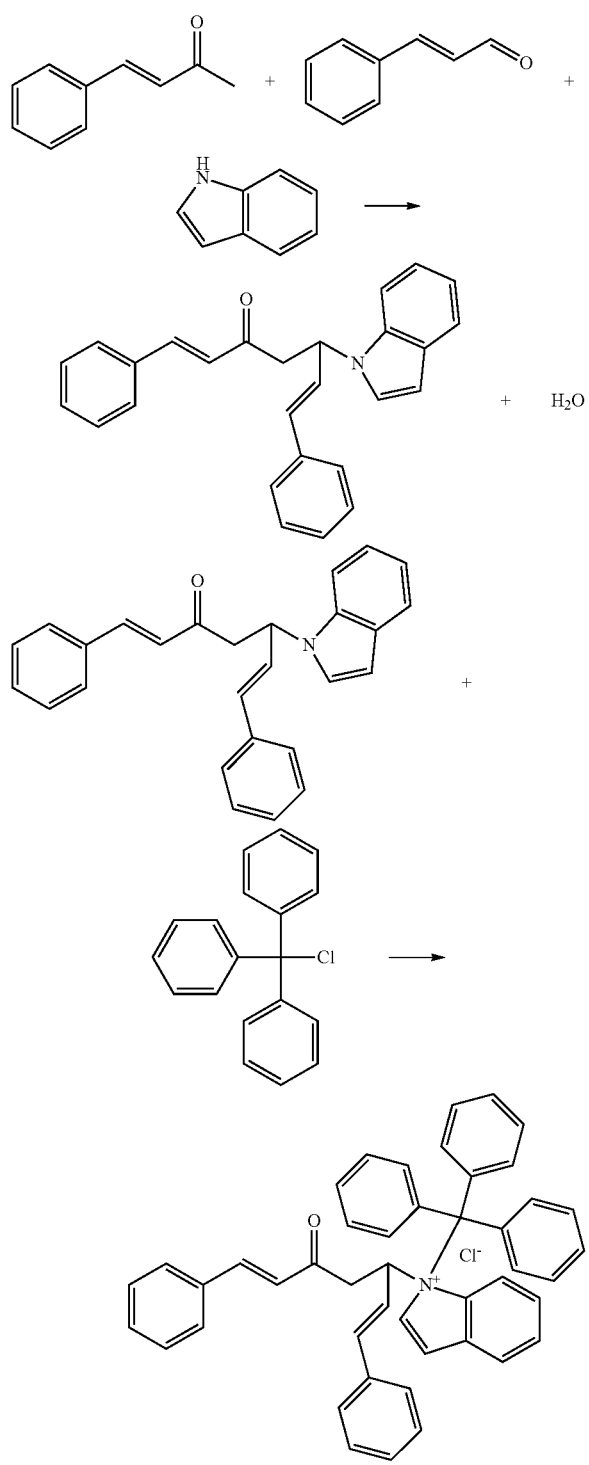

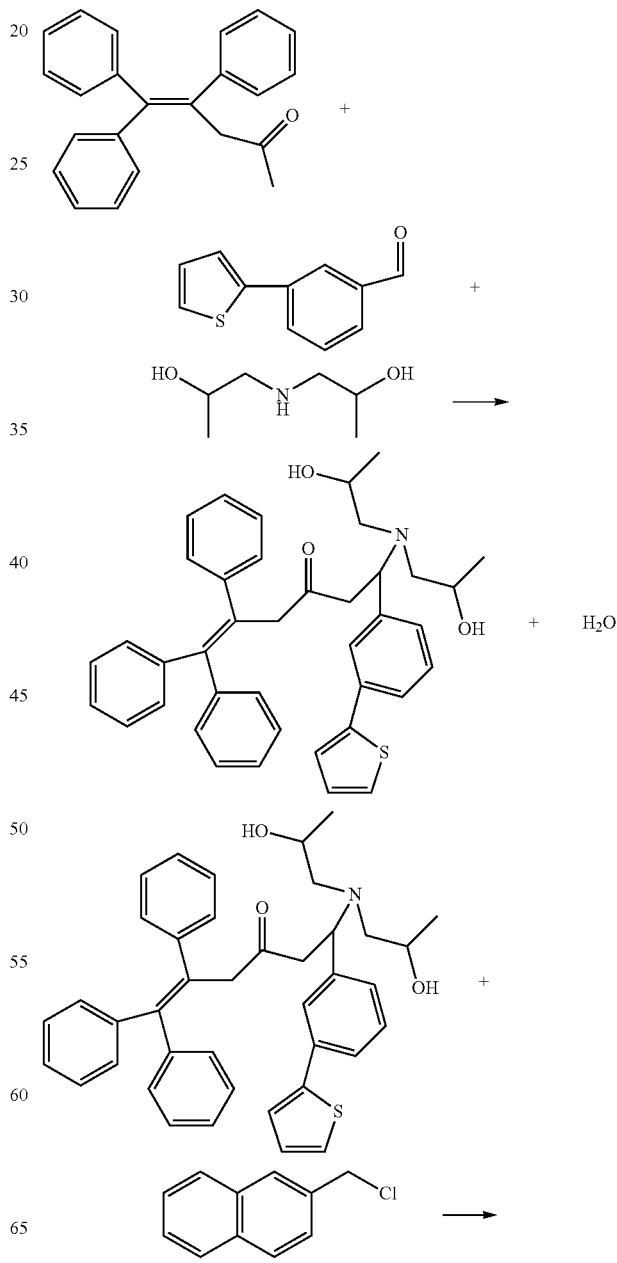

the same time and stir them well, and place the reaction system to a thermostatic water bath to react at 80° C. for 1.5 h while stirring;

(2) Add 3.12 g of diphenylstyryl acetone to the flask, adjust the pH of the reaction system to 4 using a hydrochloric acid solution, and react for 10 hours. After cooled to room temperature, remove the solvent by distillation under reduced pressure, to obtain a Mannich base;

(3) Add 6.33 g of the above Mannich base product to a 250 mL three-necked flask, add 130 mL of absolute ethanol as a solvent and stir them well, slowly add 1.76 g of chloromethylnaphthalene and stir well, and stir at 80° C. to react for 14 h, after cooled to room temperature, perform distillation under a reduced pressure to give the Mannich base quaternary ammonium salt corrosion inhibitor.

Embodiment 4

A process for preparing a Mannich base quaternary ammonium salt high-temperature resistant corrosion inhibitor, comprising the following steps:

(1) Add 1.33 g of diisopropanolamine to a 250 mL three-necked flask, then slowly add 1.88 g of 3-(2-thienyl) benzaldehyde, and add 120 mL of acetonitrile as a solvent at

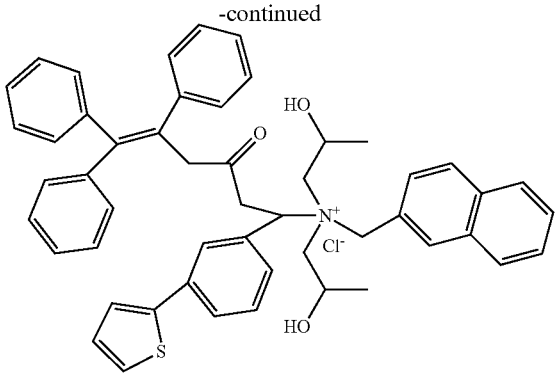

Performance Test 1 Determination of Water Solubility of Corrosion Inhibitors

The water solubility of the corrosion inhibitor prepared by Embodiments 1 to 4 and its compatibility with the system containing the iron ion stabilizer, clay stabilizer and discharge aiding agent under 90° C. are determined. The process is as follows: weigh 0.1 g of the corrosion inhibitor respectively, and dissolve in 200 mL of 20% hydrochloric acid solution, stir and observe its dissolution. Prepare 20% hydrochloric acid solution system adding with iron ion stabilizer citric acid, clay stabilizer potassium chloride and discharge aiding agent OP-10 or fluorocarbon surfactant, respectively, and then weigh 0.1 g of the corrosion inhibitor and add them to the 20% hydrochloric acid solution system, to observe the compatibility. Results are shown in the Table 1 below.

TABLE 1

Test of water solubility and compatibility of different corrosion inhibitors

| corrosion inhibitor | Water solubility | Compatibility |
|---|---|---|
| Embodiment 1 | Soluble reddish brown transparent liquid | Uniform and transparent, no layering |
| Embodiment 2 | Soluble reddish brown transparent liquid | Uniform and transparent, no layering |
| Embodiment 3 | Soluble reddish brown transparent liquid | Uniform and transparent, no layering |
| Embodiment 4 | Soluble reddish brown transparent liquid | Uniform and transparent, no layering |

As shown from table 1, the corrosion inhibitor prepared by the invention has excellent water solubility, and has good compatibility with various addition agents in a high-temperature hydrochloric acid system. The system is uniform and transparent and free of layering.

Performance Test 2 Determination of Corrosion Inhibition Performance of Corrosion Inhibitors The corrosion inhibition performance of corrosion inhibitors in the embodiments 1 to 4 is determined by a 4 h corrosion weight loss test at 90° C. using 20% hydrochloric acid as a corrosive medium and P110 carbon steels. The amount of corrosion inhibitors is 1000 ppm. Results are shown in the Table 2.

TABLE 2

Determination of corrosion inhibition performance of all corrosion inhibitors

| corrosion inhibitor | Corrosion rate ($gm^{-2}h^{-1}$) | Inhibition rate (%) | Surface morphology |
|---|---|---|---|
| Blank | 724.63 | / | Uneven |
| Embodiment 1 | 9.87 | 98.63 | Smooth and flat |
| Embodiment 2 | 14.71 | 97.96 | Smooth and flat |
| Embodiment 3 | 10.16 | 98.59 | Smooth and flat |
| Embodiment 4 | 11.47 | 98.41 | Smooth and flat |

As shown from the Table 2, the corrosion inhibitors prepared by the method of the present invention have a good corrosion inhibition effect.

In summary, the preparation process of the present invention is simple and feasible. The prepared corrosion inhibitor is ionic and has good water solubility in acid solution. The corrosion inhibitor has obvious inhibitory effect on the corrosion of carbon steels in oil-gas wells at a high temperature of 90° C.; in addition, after cleaning, the hanging pieces are flat and free of obvious pitting corrosion, indicating that the corrosion inhibitors prepared by the invention have the features of acid resistance and high-temperature resistance.

The invention claimed is:

1. A process for preparing a Mannich base quaternary ammonium salt high-temperature resistant corrosion inhibitor, comprising the following steps in sequence:
   (1) dissolve an amine substance indole, benzhydrylpiperidine, diphenylethylamine, dibenzylamine or diisopropanolamine into an organic solvent, slowly add an aldehyde substance 3-(2-thienyl)benzaldehyde or cinnamaldehyde, then place in a constant-temperature water bath, stir to react at 60-80° C. for 1 to 3 hours, then add a ketone substance benzalacetone, diphenylstyryl acetone or 1,1-diphenylacetone at a certain ratio, adjust the reaction system pH to 3 to 4 using a hydrochloric acid solution, and then react for 7 to 10 hours; after cooled to room temperature, perform distillation under a reduced pressure to remove the solvent, to obtain a Mannich base;
   (2) dissolve the Mannich base in an organic solvent, add quaternizing reagent chloromethylnaphthalene, benzyl chloride or triphenylchloromethane at a certain ratio, then react at 70-90° C. for 14-16 hours, after cooled to room temperature, perform distillation under a reduced pressure to give the Mannich base quaternary ammonium salt high-temperature resistant corrosion inhibitor.

2. The process for preparing a Mannich base quaternary ammonium salt high-temperature resistant corrosion inhibitor according to claim 1, wherein the molar ratio of amine substance, aldehyde substance and ketone substance is 1:1:1-1:1:2 in the step (1).

3. The process for preparing a Mannich base quaternary ammonium salt high-temperature resistant corrosion inhibitor according to claim 1, wherein the organic solvent is ethanol or acetonitrile.

4. The process for preparing a Mannich base quaternary ammonium salt high-temperature resistant corrosion inhibitor according to claim 1, wherein the molar ratio of Mannich base to quaternizing reagent in the step (2) is 1: 1-1:2.

* * * * *